United States Patent [19]

Stephens

[11] Plant 5,051

[45] May 10, 1983

[54] PLUM TREE

[76] Inventor: Buell K. Stephens, 19884 Avenue 324, Woodlake, Calif. 93286

[21] Appl. No.: 317,308

[22] Filed: Nov. 2, 1981

[51] Int. Cl.[3] ..... A01H 5/03
[52] U.S. Cl. ..... Plt./38
[58] Field of Search ..... Plt./38

[56] References Cited

U.S. PATENT DOCUMENTS

P.P. 2,674 10/1966 Campagne ..... Plt./38

*Primary Examiner*—Robert E. Bagwill
*Attorney, Agent, or Firm*—Huebner & Worrel

[57] ABSTRACT

A plum tree substantially identical to the Santa Rosa Plum Tree (unpatented), which it most nearly resembles, and which bears reddish-purple skinned, light yellow-fleshed, cling stone fruit, but distinguished by bearing fruit which ripens from two to three weeks earlier than the fruit of the Santa Rosa Plum Tree.

2 Drawing Figures

BACKGROUND OF THE VARIETY

The present invention relates to a new and distinct variety of plum tree which is broadly characterized by substantial identical trees and fruit to the Santa Rosa variety of plum tree (unpatented), but which is distinguished from the Santa Rosa by bearing fruit which ripens from two to three weeks earlier.

The Santa Rosa variety of plum tree is probably the most important variety of plum tree for commercial and home use, and has been the most important early ripening variety. It bears fruit which is early ripening, is of medium to large size, has flesh which is light yellow, has purplish red skin with a heavy bloom, and a rich pleasing flavor.

As with other fresh produce, the time of harvest of plums greatly influences the prices brought on the market. Generally, the earlier an early ripening plum can be marketed the higher the price, and the early ripening of fruit of the Santa Rosa variety is a substantial factor in its commercial success. It is evident, therefore, that a variety of plum tree bearing fruit, which substantially duplicates that of the Santa Rosa variety but which ripens even earlier will be highly advantageous since the fruit of such a variety can be marketed at a time when it will bring a relatively high price due to the then existing scarcity of other plums.

ORIGIN AND ASEXUAL REPRODUCTION OF THE NEW VARIETY

My new variety of plum tree was discovered by me in June, 1976 as sport growing in an orchard of Santa Rosa plum trees at my home, which is owned by me and is located at 19884 Avenue 324 near Woodlake, in the County of Tulare, in the State of California. The sport was asexually reproduced by grafting at said orchard under my supervision, and the fruit and tree characteristics resulting from such grafting proved identical to those of the original sport except for its earlier ripening.

SUMMARY OF THE NEW VARIETY

The instant variety of plum tree is characterized by perpetuating the tree and fruit characteristics of its parent, the Santa Rosa variety of plum tree, but has the important distinction of ripening from two to three weeks earlier under the growing conditions prevailing in the San Joaquin Valley of California. The fruit of the new and very early ripening variety of plum tree is of uniform and medium to large size and has a reddish-purple skin with small yellow dots. The fruit is cling stone and has light yellow, firm textured flesh.

BRIEF DESCRIPTION OF THE DRAWING

The accompanying drawing is two color photographs of mature plums of the subject variety, one photograph showing the plums growing on a representative branch and the other photograph including a plum divided to show the flesh color and three plums with the bloom substantially removed together with characteristic leaves.

DETAILED DESCRIPTION

Referring more specifically to the pomological details of the new and distinct variety of plum tree, the following has been observed under the ecological conditions prevailing in the above specified orchard near Woodlake, Tulare County, Calif. All of the color plate designations are by reference to the Maerz and Paul *Dictionary of Color,* Second Edition, 1950, published by the McGraw-Hill Book Company, Inc., common descriptive color names also being used.

TREE

Substantially similar in size, figure, productivity, bearing, and in trunk, branch, flower and bud configuration and coloration to the Santa Rosa (unpatented) plum tree.

Leaves:

*Length.*—40 to 90 mm., average about 75 mm.

*Width.*—15–35 mm., average about 25 mm.

*Shape.*—Somewhat oblanceolate; cuneate base; tips usually acute with some accuminate and a few obtuse.

*Marginal form.*—Serrulate.

*Color.*—Upper side, dark yellowish green, between Plate 23-L-10 and Plate 24-L-10; under side, moderate yellow green, Plate 23-H-5.

*Glands.*—Substantially lacking.

*Petiole.*—Length varies from 8 to 20 mm., average about 12 mm.; thickness 1½ mm.

*Stipules.*—Usually lacking, when present fine and narrow and about 5 mm. in length.

Flower: Blooms with Santa Rosa, about February 15, although fruit ripens earlier.

FRUIT

Maturity: Ready to harvest for shipment about May 30–June 1, firm, immature color, yellow-green.

Size: Uniform; medium to large; depening on thinning and other cultural practices, typical diameters: axial diameter 53 mm; transverse diameter in suture plane 52 mm; transverse diameter at right angles to suture plane 55 mm.

Form: Uniform; globose; symmetrical.

*Suture.*—Very shallow and narrow, extending between apex and stem cavity.

*Shoulders.*—Rounded, somewhat higher laterally.

*Ventral surface.*—Round, lips equal.

*Stem cavity.*—Oval with length 17 mm., width 15 mm., and depth 10 mm.

*Base.*—Flat, at right angle to axis.

*Apex.*—Slightly depressed with pistil point lacking.

*Stem.*—Length 13 mm., caliper 2 mm.

*Skin color.*—At harvest: yellow green, Plate 19-K-5, with suture and apex reddish-purple. When eating ripe: Plate 6-L-8 (Dark Cardinal) to Plate 8-L-7 (Carbuncle +) with many small dots and with small patches, both approximately Plate 11-L-6 (Brass).

*Bloom.*—At harvest: greenish-gray, Plate 17-A-4. When eating ripe: heavy and grayish-blue, Plate 33-A-7.

Flesh: Eating quality similar to Santa Rosa; firm texture with fibers lacking; uniform whitish-yellow in color, Plate 18-F-1, from skin to pit.

Stone:

*Cling characteristics.*—Cling.

*Splitting tendency.*—None observed.

*Fibers.*—None.

*Form.*—Similar to Santa Rosa, with base higher on dorsal side and nearly smooth sides.

*Size.*—Length 17 mm., width 14 mm., thickness 8 mm.

*Grooves.*—Shallow groove on dorsal side, deeper toward apex and base; pair of grooves along ventral side and individual to lateral sides, one very shallow and other substantially deeper.

*Color.*—Plate 11-J-7 (Inca Gold).

Although the new variety of plum tree possesses the described characteristics as a result of the growing conditions in Tulare County, Calif. in the San Joaquin Valley, it is to be understood that variations of the usual magnitude in characteristics incident to growing conditions, fertilization, pruning, and pest control are to be expected.

Having thus described and illustrated my new variety of plum tree, what is claimed as new and desired to be secured by Letters Patent is:

1. A new and distinct variety of plum tree substantially as illustrated and described, and characterized by trees, leaves, and fruit which are substantially identical to those of the Santa Rosa (unpatented) plum tree, but distinguished therefrom and characterized as to novelty by fruit which ripens from two to three weeks earlier than the Santa Rosa.

* * * * *

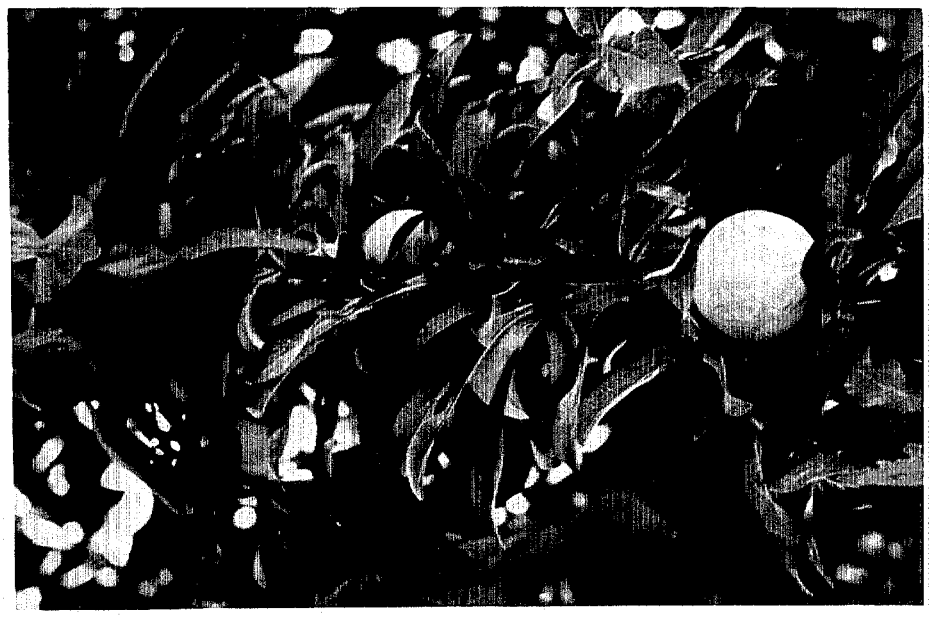
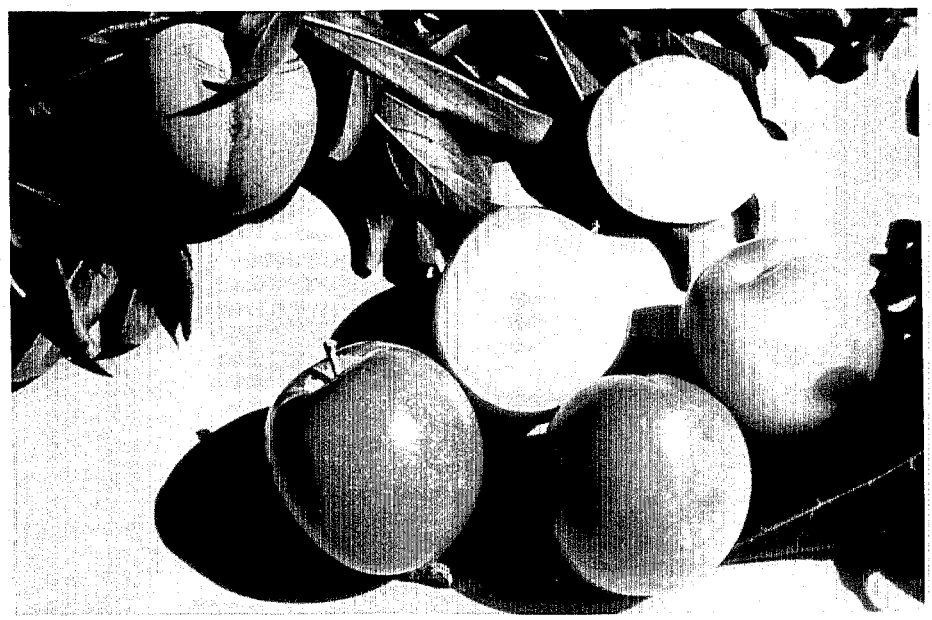

UNITED STATES PATENT AND TRADEMARK OFFICE

CERTIFICATE OF CORRECTION

PATENT NO. : PP 5051

DATED : May 10, 1983

INVENTOR(S) : Buell K. Stephens

It is certified that error appears in the above-identified patent and that said Letters Patent is hereby corrected as shown below:

Column 1, line 31, between "as" and "sport" insert ---a---.

Column 3, line 12, delete "depening" and substitute ---depending---.

Signed and Sealed this

*Twenty-sixth* Day of *July 1983*.

[SEAL]

*Attest:*

GERALD J. MOSSINGHOFF

*Attesting Officer*

*Commissioner of Patents and Trademarks*